United States Patent [19]

Kühne

[11] 4,059,436

[45] Nov. 22, 1977

[54] HERBICIDAL COMPOSITIONS CONTAINING SILYLATED CHLOROACETANILIDES

[75] Inventor: Manfred Kühne, Pfeffingen, Switzerland

[73] Assignee: Ciba-Geigy Corporation, Ardsley, N.Y.

[21] Appl. No.: 740,893

[22] Filed: Nov. 11, 1976

Related U.S. Application Data

[63] Continuation-in-part of Ser. No. 551,463, Feb. 20, 1975, Pat. No. 3,996,254.

[30] Foreign Application Priority Data

Feb. 25, 1974 Switzerland .................. 02632/74

[51] Int. Cl.$^2$ .......................................... A01N 9/20
[52] U.S. Cl. ........................................... 71/118; 71/76; 424/184; 260/448.2 N; 260/448.8 R

[58] Field of Search .................... 71/118, 76; 260/448.2 N, 448.8 R

[56] References Cited

U.S. PATENT DOCUMENTS

| | | | |
|---|---|---|---|
| 3,442,926 | 5/1969 | Houtman | 260/448.8 R |
| 3,558,683 | 1/1971 | Belsky et al. | 260/448.2 N |
| 3,651,115 | 3/1972 | Belsky et al. | 260/448.2 N |
| 3,720,699 | 3/1973 | Stoddard | 260/448.8 R |
| Re. 26,961 | 10/1970 | Hamm et al. | 71/118 |

OTHER PUBLICATIONS

Benkeser et al., "J.A.C.S.", 74, pp. 253–254 (1952).
"Chemical Abstracts", 54, p. 357h, (1960).

*Primary Examiner*—Paul F. Shayer
*Attorney, Agent, or Firm*—Harry Falber

[57] ABSTRACT

Silylated N-substituted chloroacetanilides have been found to be effective plant regulating substances, preferably selective herbicides.

10 Claims, No Drawings

HERBICIDAL COMPOSITIONS CONTAINING SILYLATED CHLOROACETANILIDES

CROSS REFERENCE

This a continuation-in-part application of application Ser. No. 551,463, filed Feb. 20, 1975 now U.S. Pat. No. 3,996,254.

The present invention relates to plant growth-regulating compositions containing new Si-containing N-substituted chloroacetanilides as active substances, as well as to processes for the selective control of weeds in cultivated crops by application of the new active substances or of compositions containing them.

Herbicidally effective haloacetanilides have already become known from the literature. Reference is made to the following patent specifications as relevant prior art: French patent specification Nos. 1,337,529, 1,419,116; Belgian patent specification Nos. 746,288; U.S. Patent Nos. 2,863,752, 3,442,945 and 3,547,620; and German Offenlegungsschriften Nos. 2,212,268, 2,305,495 and 2,328,340.

In a number of these patent specifications, relationships between herbicidal effectiveness and chemical constitution of the active substance are discussed. From this it is clear that even minute modifications of the constitution can appreciably affect the sphere of action and the usefulness of the active substance in certain cultivated crops.

Silicon-containing haloalkanoylanilides or compositions containing them as active ingredients have hitherto not been described.

The new N-substituted silyl-chloroacetanilides to be used in the compositions of this invention correspond to formula I

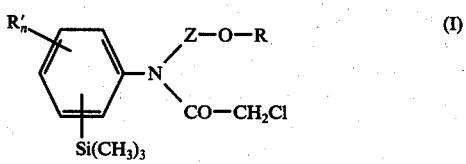

wherein

R represents a lower alkyl group having at most 4 carbon atoms, a group —CH$_2$—CH$_2$—Si(CH$_3$)$_3$, a group —CH$_2$—Si(CH$_3$)$_3$ or a trimethylsilyl group, Z represents a straight or branched alkylene chain having at most 3 carbon atoms, R' represents halogen, lower alkyl or alkoxy having at most 3 carbon atoms or trimethylsilyl, and n represents the number 0 or 1.

Among these compounds, the ones to be emphasised are those wherein n is 0, the Si(CH$_3$)$_3$ group is in the ortho position and Z represents the methylene group, such as N-methoxymethyl-2-trimethylsilyl-chloroacetanilide and the corresponding N-ethoxymethyl, N-propoxymethyl and N-isopropoxymethyl analogues.

The new active substances of formula I may be manufactured by a process in which a substituted aniline of formula II

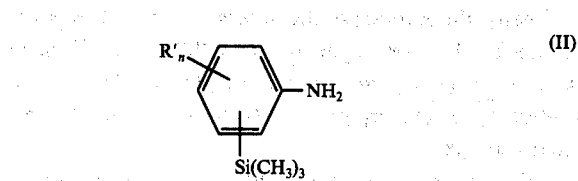

is reacted with an aldehyde or ketone of the formula

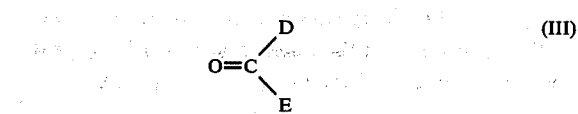

to a Schiff base of the formula

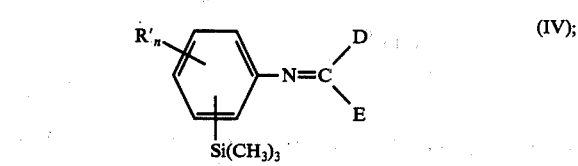

to the double bond there is then added a chloroacetyl halide

Hal — CO — CH$_2$ — Cl with the formation of a product of formula V

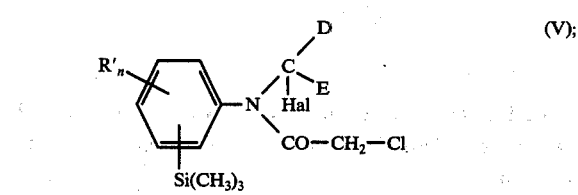

and this is subsequently reacted with an alcohol of the formula HO—R, in the presence of a base, to give the final product of formula I.

In the preceding formulae, Hal represents a halogen atom, preferably chlorine or bromine, and D and E each represent hydrogen, or monovalent aliphatic hydrocarbon radicals which constitute together with the C-atom to which they are bound the radical —Z—OR or a precursor thereof.

The meanings of the remaining substituents R, R' and n correspond to the definition given for formula I.

A variant of this process is a procedure whereby the Schiff base of formula IV is catalytically hydrogenated and the formed secondary amine is acylated by reaction with a chloroacetyl halide.

Preferably used as Compound III is formaldehyde in the form of paraformaldehyde.

The first reaction step to give the Schiff base is preferably performed at normal pressure, at temperatures of 50° - 120° C in the presence of tertiary amines such as trimethylamine, in such organic solvents which render possible the removal by azeotropic distillation of the water formed during the reaction (e.g. benzene, toluene, etc.). There is formed in the process principally the trimer of the Schiff base. Chloroacetylation is performed advantageously under normal pressure at —20° to +150° C in aprotic solvents from the hydrocarbon series, such as benzene and toluene.

Finally, the reaction of the product of formula V with an alcohol HO—R is performed at 20° - 150° C, likewise in aprotic solvents such as benzene or toluene, and preferably in the presence of tertiary amines such as triethylamine.

A further process by which the new active substances of formula I can be obtained is one wherein there is introduced into the initial aniline of formula II the group —Z—O—R by means of a compound splitting off this group, e.g. an alkyl halide or p-toluenesulphonic acid ester; and the intermediate of formula VI

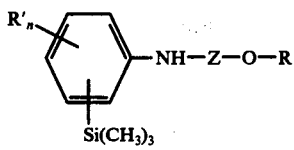 (VI)

is thereupon acylated, as described above, with a chloroacetyl halide.

In a further process, a nucleus-halogenated aniline derivative of the formula

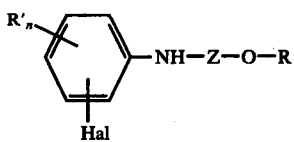 (VII)

is used as the starting material; this is converted with two moles of butyl-lithium into the compound of the formula

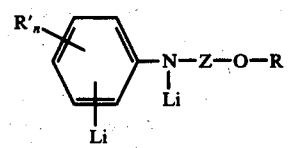 (VIII);

this is then doubly silylated by reaction with halotrimethylsilane Hal—Si(CH$_3$)$_3$ with the splitting-off of 2 moles of LiHal; the trimethylsilyl group on the nitrogen atom is afterwards split off by saponification; and the resulting intermediate of formula VI is acylated with chloroacetyl halide as described above.

Finally, the end products of formula I wherein the alkylene chain Z contains at least two carbon atoms are obtained also by a process in which the starting aniline of formula II is monoacylated with an acid halide of formula IX

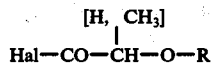 (IX), wherein R has the meaning given under formula I; the —CO— group is then hydrogenated with a metal hydride, preferably LiAlH$_4$, to give the intermediate of formula X

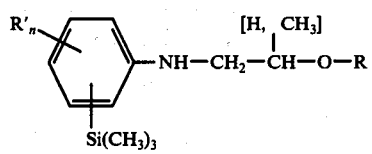 (X);

and the last-mentioned is subsequently acylated with a chloroacetyl halide to obtain the desired final product. Formula X embraces a number of compounds of formula VI. Intermediates of formula VI wherein Z represents a straight or branched alkylene chain having at least 2 carbon atoms can be formed also by condensation of the substituted aniline II with a carbonyl compound XI

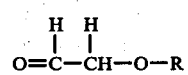 (XI)

in which one of the hydrogen atoms shown isolated can also represent a CH$_3$ group; and simultaneous or subsequent catalytic hydrogenation of the azomethine thus obtained.

All reactions can be performed in the presence or absence of solvents or diluents inert to the reactants. The following are, for example, suitable: aliphatic, aromatic or halogenated hydrocarbons such as benzene, toluene, xylenes, petroleum ether and ethereal compounds such as dialkyl ether, dioxane or tetrahydrofuran, as well as mixtures of these solvents with each other.

Suitable chloroacetylation agents used are chloroacetyl halides, preferably chloroacetyl chloride or chloroacetyl bromide. The reaction temperatures are between −30° C and +200° C, preferably between −15° C and +80° C. Chloroacetylation is preferably performed in the presence of an acid-binding agent. Suitable as such are tertiary amines such as trialkylamines, e.g. triethylamine, pyridine and pyridine bases, or inorganic bases such as the oxides, hydroxides, hydrogen carbonates and carbonates of alkali metals and alkaline-earth metals. As an acid-binding agent, it is also possible to use the respective aniline of formula II, VI or X, which in this case has to be used in excess.

Starting materials of formula II are in some cases known: for instance, the three isomeric trimethylsilylanilines have been described in the Journal Am.-Chem. Soc. 74, p. 253 (1952). Further corresponding starting materials of this formula II can be easily produced in an analogous manner, and from these likewise the Schiff bases of formula IV and the compounds of formulae VI and X serving as intermediates or starting materials. The starting materials of formula VII are also known.

The following example illustrates the production, according to the invention, of a new active substance of formula I. Further active substances, which have been produced by one of the described processes, are given in the following table. Temperatures are in degrees Centigrade.

The resulting final products are soluble in the usual organic solvents and have good stability.

EXAMPLE 1 a. 49.6 g of 2-trimethyl-silyl-aniline, 12.6 g of paraformaldehyde and 3 ml of a 40% aqueous solution of trimethylamine are boiled in 300 ml of toluene in a water separator until no further water is being separated.

The contents of the flask are concentrated in a rotary evaporator and subsequently distilled in vacuo. There passes over at 20 Torr and 105°–125° a mixture of monomeric and trimeric 2-trimethylsilyl-phenyl-N-methylene-amine.

The distillate crystallises after some time almost completely with formation of the trimer. This has a melting point of 128°–130°, and exhibits in the NMR-spectrum a singulet at approx. 4.4 ppm (6H) in addition to the signals to be expected at 7.5 ppm (multiplet, 12H) and 0.3 ppm (singulet, 27H). Hence the hexahydrotriazine structure of the crystals is proved.

b. 169.5 g of chloroacetyl chloride is placed into 150 ml of anhydrous benzene, and there is added dropwise with cooling a solution of 266 g of the Schiff base, produced according to (a), dissolved in 150 ml of anhydrous benzene. It is permissible for the temperature during the addition to rise to 60°. After completion of the dropwise addition, the mixture is stirred for a further hour with refluxing and then cooled to about +50°. An addition is made at this temperature of 187.5 ml of anhydrous methanol, and the mixture is then brought to boiling. The heating bath is removed and 159 g of anhydrous triethylamine is added dropwise. The reaction occurring at this point is intensely exothermic. The intensity of boiling can be easily kept under control by regulation of the dropping rate.

After the addition of amine is completed, stirring is continued for about 15 minutes at the reflux temperature. The solvent is afterwards evaporated off as far as possible and ether and water are added to the pasty substance remaining. The separated ether phase is washed three times with water, then dried and concentrated by evaporation. The oil remaining after complete removal by evaporation of the ether is pure N-chloroacetyl-N-methyloxymethyl-2-trimethylsilyl-aniline, $n_D^{20}$ = 1.5343, B.P. 135°–137°/0.6 Torr.

| Analysis: | C | cal. | 34.7 | found | 54.8 % |
|---|---|---|---|---|---|
| | H | " | 7.05 | " | 6.9 % |
| | N | " | 4.90 | " | 5.1 % |

After prolonged standing, the substance crystallises, M.P. 40–45°.

Table I

Compounds of the formula

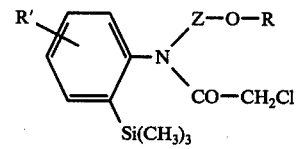

| Compound No. | Z | R | R' | Physical data |
|---|---|---|---|---|
| 1 | —CH$_2$— | CH$_3$ | H | M.P. 40–45°; B.P. = 135–137°/0.6 Torr |
| 2 | —CH$_2$— | C$_2$H$_5$ | H | B.P. 85–88°/0.005 Torr |
| 3 | —CH$_2$— | n-C$_3$H$_7$ | H | B.P. 106°/0.015 Torr |
| 4 | —CH$_2$— | i-C$_3$H$_7$ | H | B.P. 115–117°/0.25 Torr |
| 5 | —CH$_2$— | n-C$_4$H$_9$ | H | B.P. 125°/0.01 Torr |
| 6 | —CH$_2$—CH$_2$— | CH$_3$ | H | |
| 7 | —CH$_2$—CH$_2$— | C$_2$H$_5$ | H | oil |
| 8 | —CH$_2$—CH$_2$— | C$_3$H$_7$ | H | oil |
| 9 | —CH$_2$—CH$_2$— | -n-C$_4$H$_9$ | H | |
| 10 | —CH—CH$_2$—<br>\|<br>CH$_3$ | CH$_3$ | H | |
| 11 | —CH—CH$_2$—<br>\|<br>CH$_3$ | C$_2$H$_5$ | H | viscous oil |
| 12 | —CH—CH$_2$—<br>\|<br>CH$_3$ | C$_3$H$_7$ | H | viscous oil |
| 13 | —CH—CH$_2$—<br>\|<br>CH$_3$ | n-C$_4$H$_9$ | H | |
| 14 | —CH$_2$— | CH$_3$ | p-Si(CH$_3$)$_3$ | |
| 15 | —CH$_2$— | C$_2$H$_5$ | p-Si(CH$_3$)$_3$ | |
| 16 | —CH$_2$— | i-C$_3$H$_7$ | p-Si(CH$_3$)$_3$ | |
| 17 | —CH$_2$— | CH$_3$ | o-Si(CH$_3$)$_3$ | |
| 18 | —CH$_2$— | C$_2$H$_5$ | o-Si(CH$_3$)$_3$ | |
| 19 | —CH$_2$— | i-C$_3$H$_7$ | o-Si(CH$_3$)$_3$ | |
| 20 | —CH$_2$— | —Si(CH$_3$)$_3$ | H | |
| 21 | —CH$_2$ | —CH$_2$—Si(CH$_3$)$_3$ | H | B.P. 145°/0.01 Torr |
| 22 | —CH$_2$— | —(CH$_2$)$_2$—Si(CH$_3$)$_3$ | | |

The active substances according to the invention are stable compounds and they have, particularly before emergence of the plants, very good herbicidal properties against Gramineae such as millet and millet-like plants of the genera Setaria, Echinochloa, Digitaria etc., against Cyperaceae, against grasses such as Lolium species and wild oats, and also against many dicotyledonous species of weeds such as Amaranthus, Sesbania, Datura, Chrysanthemum, Ipomoea, Galium, Sinapis, Pastinaca, etc., without the cultivated plants for which the active substance is being used suffering damage. Cultivated plants that may be mentioned are, in particular, soya bean, cotton, maize, alfalfa, sugar beet and sunflower, as well as varieties of cereals such as barley and wheat. Compounds having a branched alkylene chain Z have fungicidal action against phytopathogenic fungi.

The active substances are applied either before or after emergence of the cultivated plants and weeds and wild grasses, preferably before emergence. The amounts applied are between 0.1 and 10 kg of active substance per hectare; in the case of pre-emergence, however, an extensive destruction of weeds is achieved already with an applied amount of 0.25 kg/hectare. In order to prevent weed infestation of railway embankments, factory sites, roads, etc., the amount used is usually up to 10 kg of active substance per hectare.

Furthermore, some of the new active substances of formula I exhibit with post-emergence application growth-regulating properties: they retard or inhibit, for example, the growth in height of monocotyledonous plants, and prevent the premature germination of stored seed and tubers.

Tests have shown that in the pre-emergence process the compounds in the table, applied in amounts of 1 – 2 kg per hectare, which amounts are important with regard to application, have an excellent action against the weeds *Avena fatua, Lolium perenne, Alopecurus myos., Setaria italica, Rottboellia exelt., Digitaria sang., Echinochloa crus galli, Cyperus esculentus,* Leptochloa, *Poa trivialis, Sinapis alba,* Galinsoga, Amaranthus, Datura, etc.; at the same time, however, they damage the cultivated plants maize, cotton, sugar beet, soya bean as well as vegetables to a lesser extent than the known active substances 2,6-diethyl-N-(methoxymethyl)-chloroacetanilide and 2,6-dimethyl-N-(methoxyethyl)-chloroacetanilide. The compounds in which —Z—OR represents a silicon-containing substituent have good compatibility with rice crops and cultivated sorghum, whilst simultaneously combatting the accompanying weeds.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms: Solid forms:

dusts, tracking agents, granules, coated granules, impregnated granules and homogeneous granules.
Liquid forms:
a. active substances which are dispersible in water: wettable powders, pastes, emulsions;
b. solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomacous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nut-shell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.5% to 80% by weight.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation products of urea and formaldehyde, and also latex products. Preferred dispersion (suspensions and emulsions) are manufactured by mixing or grinding the active substance with carriers accompanied by the addition of dispersing agents and solvents, in the process of which there result firstly dispersible active substance concentrations, such as wettable powders and emulsifiable concentrates.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5–80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salt of oleoyl methyl tauride, ditertiary acetalene glycols, dialkyl dilauryl ammonium chloride and fatty acid alkali and alkaline earth metal salts.

Suitable anti-foam agents are silicones.

The active substance is so mixed, ground sieved and strained with the additives mentioned above that, in wettable powders, the solid particle size of from 0.02 to 0.04 mm and in pastes, of 0.03 mm is not exceeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulphoxide, and mineral oil fractions boiling between 120° and 350° C. The solvents must be practically odorless, not phytotoxic, inert to the active substances and not readily inflammble.

Furthermore, the agents according to the invention can be applied in the form of solutions. For this purpose the active substances or several active substances of general formula I are dissolved in suitable organic solvents or mixtures of solvents with water. Aliphatic and aromatic hydrocarbons, chlorinated derivatives thereof, alkyl naphthalenes and mineral oils singly or in admixture, can be used as organic solvents. The solutions contain the active substance in a concentration range from 1% to 20%.

In addition to fungicidal active substances, the agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited active substance of the formula I. The agents according to the invention may also contain plant fertilisers, trace elements, other herbicides etc. Preparations of the new active substances of the general formula I are described in the following. The term 'parts' denotes parts by weight.

GRANULES

The following substances are used to produce a 5% granule:
5: parts of N-(ethoxymethyl)-2-trimethylsilyl-chloroacetanilide
0.25: part of epichlorohydrin,
0.25: part of cetyl polyglycol ether,
3.50: parts of polyethylene glycol,
91: parts of kaolin (particle size 0.3 - 0.8 mm).

The active substance is mixed with epichlorohydrin and dissolved in 6 parts of acetone; the polyethylene glycol and cetyl polyglycol ether are then added. The solution thus obtained is sprayed on to kaolin, and the acetone is subsequently evaporated off in vacuo.

WETTABLE POWDER

The following constituents are used to produce (a) a 50%, (b) a 25% and (c) a 10% wettable powder:

(a)

50: parts of N-(2'-methoxyethyl)-2-trimethylsilyl-chloroacetanilide,
5: parts of sodium dibutyl-naphthalene sulphonate,
3: parts of naphthalenesulphonic acid/phenolsulphonic acid/formaldehyde condensate 3:2:1,
20: parts of kaolin,
22: parts of Champagne chalk;

(b)

25: parts of N-trimethylsilylmethoxymethyl)-2-trimethylsilyl-chloroacetanilide,
5: parts of the sodium salt of oleyl methyl tauride,
2.5: parts of naphthalenesulphonic acid/formaldehyde condensate,
0.5: part of carboxymethylcellulose,
5: parts of neutral potassium aluminium silicate,
62: parts of kaolin;

(c)

10: parts of N-(methoxymethyl)-2- trimethylsilyl-chloroacetanilide,
3: parts of a mixture of the sodium salts of saturated fatty alcohol sulphates, 5: parts of naphthalenesulphonic acid/formaldehyde condensate.
82: parts of kaolin.

The given active substance is absorbed onto the appropriate carriers (kaolin and chalk), and the whole is subsequently mixed and ground. There are obtained wettable powders having excellent wettability and suspension properties. It is possible to produce from such wettable powders, by dilution with water, suspensions of any desired concentration.

PASTE

The following substances are used to produce a 45% paste:
45: parts of N-(isopropoxymethyl)-2-trimethylsilyl-chloroacetanilide,
5: parts of sodium aluminium silicate,
14: parts of cetyl polyglycol ether having 8 moles of ethylene oxide,
1: part of oleyl polyglycol ether having 5 moles of ethylene oxide,
2: parts of spindle oil,
10: parts of polyethylene glycol,
23: parts of water.

The active substance is intimately mixed with the additives in a suitable apparatus. There is obtained a paste from which can be produced, by dilution with water, suspensions of any desired concentration.

EMULSION CONCENTRATE

The following ingredients are mixed together to produce a 25% emulsion concentrate:
25: parts of N-(methoxymethyl-2-trimethylsilyl-chloroacetanilide,
5: parts of a mixture of nonyl phenol polyoxyethylene and calcium dodecyl benzenesulphonate,
35: parts of 3,5,5-trimethyl-2-cyclohexen-1-one,
35: parts of dimethylformamide. This concentrate can be diluted with water to obtain emulsions of suitable concentration. Such emulsions are suitable for the control of weeds in cultivated crops.

EXAMPLE 2

Broad action against dicotyledonous weeds and undesirable grasses in selected cultures of useful plants (preemergence method)

Immediately after the test plants have been sown in seed dishes, the active substances are applied to the surface of the soil as an aqueous suspension (obtained from a 25% wettable powder) so as to correspond to rates of application of 4 kg, 2 kg and 1 kg per hectare. The seed dishes are then kept at 22° to 23° C and 70% relative humidity. The test is evaluated according to the following linear rating.
9 = plants undamaged (as control test)
1 = plants destroyed
8 — 2 = intermediate stages of damage
— = not tested
The following haloacetanilide known from U.S. patent 3,547,620 was used as comparative compound:
compound A = 2,6-diethyl-N-(methoxymethyl)-chloroacetanilide (commercial product Alachlor)

Table 2

| Comp. Nr. | Rate of application in kg/ha | Sinapis | Chrysanthemum | Amaranthus | Echinochloa | Setaria | Digitaria | Rottboellia | Cyperus | Alopecurus | Lolium | Avena | sugar beet | cotton | soya |
|---|---|---|---|---|---|---|---|---|---|---|---|---|---|---|---|
|   | 4 | 2 | 1 | 1 | 1 | 1 | 1 | 1 | 1 | 1 | 1 | 1 | — | — | 8 |
| 1 | 2 | 2 | 1 | 1 | 1 | 1 | 1 | 1 | 1 | 1 | 1 | 1 | — | — | 8 |
|   | 1 | 2 | 2 | 1 | 1 | 1 | 1 | 1 | 1 | 1 | 1 | 2 | — | — | 9 |
|   | 4 | 2 | 2 | 1 | 1 | 1 | 1 | 1 | 1 | 1 | 1 | 1 | — | 7 | 8 |
| 2 | 2 | 2 | 3 | 2 | 1 | 1 | 1 | 1 | 1 | 1 | 1 | 2 | — | 7 | 8 |
|   | 1 | 2 | 3 | 2 | 1 | 1 | 1 | 1 | 1 | 1 | 1 | 2 | — | 8 | 9 |
|   | 4 | 2 | 2 | 1 | 1 | 1 | 1 | 1 | 1 | 1 | 1 | 1 | 7 | 8 | 7 |
| 3 | 2 | 3 | 2 | 1 | 1 | 1 | 1 | 1 | 1 | 1 | 1 | 2 | 8 | 9 | 8 |
|   | 1 | 4 | 4 | — | 1 | 1 | 1 | 1 | 1 | 1 | 1 | 2 | 9 | 9 | 9 |
|   | 4 | 2 | 2 | 1 | 1 | 1 | 1 | 1 | 1 | 1 | 1 | 1 | — | 7 | 7 |
| 4 | 2 | 2 | 4 | 2 | 1 | 1 | 1 | 2 | 1 | 1 | 2 | 1 | — | 8 | 7 |
|   | 1 | 4 | 4 | 3 | 1 | 1 | 1 | 2 | 1 | 1 | 2 | 2 | — | 9 | 9 |
|   | 4 | — | 2 | 1 | 1 | 1 | 1 | 2 | 1 | 1 | 3 | 2 | 8 | 9 | 8 |
| 5 | 2 | — | 3 | 2 | 1 | 1 | 1 | 3 | 1 | 1 | 3 | 3 | 9 | 9 | 9 |
|   | 1 | — | 5 | 5 | 1 | 1 | 1 | 5 | 1 | 2 | 3 | 3 | 9 | 9 | 9 |
|   | 4 | 6 | — | 1 | 1 | 1 | 1 | 4 | 1 | 1 | 1 | 2 | 3 | 7 | 8 |
| A | 2 | 6 | — | 1 | 1 | 1 | 1 | 4 | 1 | 2 | 2 | 2 | 4 | 9 | 8 |
|   | 1 | 6 | — | 1 | 1 | 1 | 1 | 5 | 1 | 2 | 2 | 2 | 6 | 9 | 9 |

EXAMPLE 3

Growth inhibition in grasses (postemergence method)

Seeds of the grasses Lolium perenne, Poa pratensis, Festuca ovina, and Dactylis glomerata were sown in plastic dishes filled with an earth/turf/sand mixture. After 3 weeks the germinated grasses were cut back to a height of 4 cm above the soil and 2 days later sprayed with aqueous spray broths of active substances of the formula I. The amount of active substance corresponded to a rate of application of 5 kg of active substance per hectare. Fourteen days after application the growth of the grasses was evaluated according to the following linear rating:

1 = strong inhibition (no growth from the time of application)
9 = no inhibition (growth as untreated control)

With the compounds of Formula I significant growth retardations were achieved, preferably with compounds 2 to 5, 7, 8, 11, 12 and 21 (notes 1, 2 or 3).

What I claim is:

1. A plant growth regulating agent containing as active ingredient an effective amount of a silylated chloroacetanilide of formula I

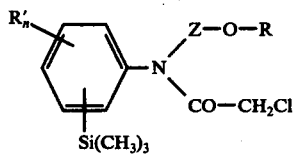

wherein
R represents a lower alkyl group having at most 4 carbon atoms, a group —CH$_2$—CH$_2$—Si(CH$_3$)$_3$, a group —CH$_2$—Si(CH$_3$)$_3$ or a trimethylsilyl group, Z represents a straight or branched alkylene chain having at most 3 carbon atoms,
R' represents halogen, lower alkyl or alkoxy having at most 3 carbon atoms or trimethylsilyl, and
n represents the number 0 or 1, together with a suitable carrier.

2. An agent according to claim 1 wherein in formula I n is 0, the Si(CH$_3$)$_3$ group is in the ortho position with respect to the amino group, and Z represents the methylene group.

3. An agent according to claim 1 containing as active ingredient N-methoxymethyl-2-trimethylsilyl-chloroacetanilide.

4. An agent according to claim 1 containing as active ingredient N-ethoxymethyl-2-trimethylsilyl-chloroacetanilide.

5. An agent according to claim 1 containing as active ingredient N-n-propoxymethyl-2-trimethylsilyl-chloroacetanilide.

6. An agent according to claim 1 containing as active ingredient N-isopropoxy-2-trimethylsilyl-chloroacetanilide.

7. An agent according to claim 1 containing as active ingredient N-n-butoxymethyl-2-trimethylsilyl-chloroacetanilide.

8. An agent according to claim 1 containing as active ingredient N-(trimethylsilylmethoxymethyl)-2-trimethylsilyl-chloroacetanilide.

9. A process for regulating plant growth which comprises applying to the plants or to their habitat an effective amount of a silylated chloroacetanilide of formula I of claim 1.

10. A process for selectively controlling weeds in cultivated crops, wherein the corresponding area is treated before emergence of the weeds with an effective amount of a silylated chloroacetanilide of formula I of claim 1.

* * * * *